US011406319B2

(12) United States Patent
Polonen et al.

(10) Patent No.: US 11,406,319 B2
(45) Date of Patent: Aug. 9, 2022

(54) METHODS AND DEVICES USING SWALLOWING ACCELEROMETRY SIGNALS FOR SWALLOWING IMPAIRMENT DETECTION

(71) Applicant: SOCIETE DES PRODUITS NESTLE S.A., Vevey (CH)

(72) Inventors: Harri Polonen, Tampere (FI); Juha Pajula, Tampere (FI)

(73) Assignee: Societe des Produits Nestle S.A., Vevey (CH)

( * ) Notice: Subject to any disclaimer, the term of this patent is extended or adjusted under 35 U.S.C. 154(b) by 304 days.

(21) Appl. No.: 16/488,440

(22) PCT Filed: Feb. 27, 2018

(86) PCT No.: PCT/EP2018/054747
§ 371 (c)(1),
(2) Date: Aug. 23, 2019

(87) PCT Pub. No.: WO2018/158218
PCT Pub. Date: Sep. 7, 2018

(65) Prior Publication Data
US 2020/0060606 A1   Feb. 27, 2020

Related U.S. Application Data

(60) Provisional application No. 62/464,849, filed on Feb. 28, 2017.

(51) Int. Cl.
*A61B 5/00* (2006.01)
(52) U.S. Cl.
CPC .......... *A61B 5/4205* (2013.01); *A61B 5/7267* (2013.01)

(58) Field of Classification Search
CPC ... A61B 5/4205; A61B 5/1123; A61B 5/7267; A61B 5/7264; A61B 5/11; A61B 5/6822;
(Continued)

(56) References Cited

U.S. PATENT DOCUMENTS

| | | | | |
|---|---|---|---|---|
| 7,749,177 B2* | 7/2010 | Chau | .................... | A61B 5/7264 600/593 |
| 2013/0184538 A1* | 7/2013 | Lee | ....................... | A61B 5/1123 600/301 |

FOREIGN PATENT DOCUMENTS

| | | |
|---|---|---|
| JP | 2014503330 A | 2/2014 |
| WO | 2012103625 A1 | 8/2012 |
| WO | 2015154960 A1 | 10/2015 |

OTHER PUBLICATIONS

Nikjoo et al. "Automatic discrimination between safe and unsafe swallowing using a reputation-based classifier" BioMedical Engineering Online, 2011, vol. 10, No. 100, 17 pages.
(Continued)

*Primary Examiner* — Deborah L Malamud
(74) *Attorney, Agent, or Firm* — K&L Gates LLP

(57) ABSTRACT

A method classifies vibrational data acquired for a swallowing event to identify a possible swallowing impairment in a candidate. The method includes receiving axis-specific vibrational data for an anterior-posterior (A-P) axis and a superior-inferior (S-I) axis and representative of the swallowing event, for example from a sensor operatively coupled to a processing module that is a local or remote computing device. A portion of the axis-specific vibrational data for the A-P axis can be combined with a portion of the axis-specific vibrational data for the S-I axis on the processing module using one or more of linear combination, squared (power) sum, moving window correlation of the two signals, local minimum or local maximum of the two signals, and trigonometric relation. The method can include outputting from
(Continued)

the processing module a classification of the swallowing event based on the combined vibrational data.

12 Claims, 3 Drawing Sheets

(58) Field of Classification Search
CPC ....... A61B 5/486; A61B 5/7282; A61B 5/394; A61B 5/4836; A61B 5/1121; A61B 5/7455; A61B 5/1126; A61B 2505/09; A61B 5/1107; A61B 5/4082; A61N 1/36031; A61N 1/36103; A61N 1/36067; A61N 1/36014
See application file for complete search history.

(56) References Cited

OTHER PUBLICATIONS

Merey et al. "Quantitative classification of pediatric swallowing through accelerometry" Journal of NeuroEngineering and Rehabilitation, 2012, vol. 9, No. 34, 8 pages.
Mamun et al. "Swallowing accelerometry signal feature variations with sensor displacement" Medical Engineering and Physics, 2015, vol. 37, pp. 665-673.
Japan Patent Office Communication for Application No. 2019-544674, Dispatch No. 751412, dated Oct. 26, 2021, 8 pages.

* cited by examiner

METHODS AND DEVICES USING SWALLOWING ACCELEROMETRY SIGNALS FOR SWALLOWING IMPAIRMENT DETECTION

CROSS REFERENCE TO RELATED APPLICATIONS

The present application is a National Stage of International Application No. PCT/EP2018/054747, filed on Feb. 27, 2018, which claims priority to U.S. Provisional Patent Application No. 62/464,849, filed on Feb. 28, 2017, the entire contents of which are being incorporated herein by reference.

BACKGROUND

The present disclosure generally relates to methods and devices for swallowing impairment detection, whereby a candidate executes one or more swallowing events and dual axis accelerometry data is acquired representative thereof. More specifically, the present disclosure relates to methods and devices that use an anterior-posterior (A-P) signal together with a superior-inferior (S-I) signal, preferably by combining the two signals by at least one process selected from the group consisting of linear combination of the two signals, squared (power) sum of the two signals, moving window correlation of the two signals, local minimum or local maximum of the two signals, and trigonometric relation between the two signals.

Dysphagia is characterized by impaired involuntary motor control of swallowing process and can cause "penetration" which is the entry of foreign material into the airway. The airway invasion can be accompanied by "aspiration" in which the foreign material enters the lungs and can lead to serious health risks.

The three phases of swallowing activity are oral, pharyngeal and esophageal. The pharyngeal phase is typically compromised in patients with dysphagia. The impaired pharyngeal phase of swallowing in dysphagia is a prevalent health condition (38% of the population above 65 years) and may result in prandial aspiration (entry of food into the airway) and/or pharyngeal residues, which in turn can pose serious health risks such as aspiration pneumonia, malnutrition, dehydration, and even death. Swallowing aspiration can be silent (i.e., without any overt signs of swallowing difficulty such as cough), especially in children with dysphagia and patients with acute stroke, rendering detection via clinical perceptual judgement difficult.

The current gold standard for tracking swallowing activities is videofluoroscopy that enables clinicians to monitor barium-infused foodstuff during swallowing via moving x-ray images. However, the videofluoroscopy swallowing study (VFSS) cannot be done routinely due to the expensive procedure and the need for specialized personnel, as well as the excessive amount of harmful radiations. Another invasive assessment is the flexible endoscopic evaluation of swallowing, which also requires trained personnel and entails an expensive procedure. Non-invasive alternatives for swallow monitoring include surface electromyography, pulse oximetry, cervical auscultation (listening to the breath sounds near the larynx) and swallowing accelerometry.

Despite introduction of different non-invasive approaches, a reliable bedside detection of swallowing abnormalities remains a challenging task. For example, a recent systematic review of cervical auscultation studies suggests that the reliability of the approach is insufficient and it can not be used as a stand-alone instrument to diagnose dysphagia. Lagarde, Marloes L J and Kamalski, Digna M A and van den Engel-Hoek, Lenie, "The reliability and validity of cervical auscultation in the diagnosis of dysphagia: A systematic review," Clinical Rehabilitation 30(2):1-9 (March 2015). Furthermore, perceptual clinical screening of dysphagia has been shown to lack agreement between different speech-language pathologists, possibly due to the subjective nature of the judgement as well as the presence of variety of environmental artifacts.

Over the past two decades, researchers have reported on various swallowing screening tools, among which those driven by swallowing sounds are the most popular. Swallowing sounds are either captured acoustically using a microphone or mechanically using an accelerometer placed on the patient's neck measuring cervical epidermal vibrations. Reports on discriminative analysis of swallowing auscultation signals vary in terms of the screening tool used, target swallowing problem (aspiration, penetration, pharyngeal residue), sample size, patient population and medical conditions, and validation approach, which makes a direct comparison between these studies virtually impossible.

Swallowing accelerometry harnesses the hyoid and laryngeal movements during swallowing activities, which are manifested as epidermal vibrations measurable at the neck by an accelerometer. Vibrations in both the anterior-posterior (A-P) and superior-inferior (S-I) anatomical directions are found to contain distinct information about the underlying swallowing activities.

Nevertheless, the development of a fully automated, accurate swallowing screening tool remains an elusive challenge.

SUMMARY

In a general embodiment, the present disclosure provides a device for identifying a possible swallowing impairment in a candidate during execution of a swallowing event. The device comprises: an accelerometer configured to acquire axis-specific vibrational data along an anterior-posterior (A-P) axis and a superior-inferior (S-I) axis of the candidate's throat, the axis-specific vibrational data is representative of the swallowing event; and a processing module that is a local or remote computing device operatively coupled to the accelerometer, the processing module configured for processing the axis-specific data to (i) combine at least a portion of a first signal comprising the axis-specific vibrational data acquired along the A-P axis with at least a portion of a second signal comprising the axis-specific vibrational data acquired along the S-I axis using at least one process selected from the group consisting of linear combination, squared (power) sum, moving window correlation of the two signals, local minimum or local maximum of the two signals, and trigonometric relation and (ii) classify the swallowing event as one of a plurality of classifications based on the combined vibrational data, the plurality of classifications comprising a first classification indicative of normal swallowing and a second classification indicative of possibly impaired swallowing.

In an embodiment, the processing module is configured to extract meta-features from the combined vibrational data. The processing module can be configured to use the meta-features extracted from the combined vibrational data to classify the swallowing event, for example by comparing the meta-features extracted from the combined vibrational data to preset classification criteria to classify the swallowing event. The preset classification criteria can be defined for each of swallowing safety and swallowing efficiency and/or defined by features previously extracted and classified from a known training data set.

In an embodiment, the second classification is indicative of at least one of a swallowing safety impairment or a swallowing efficiency impairment.

In an embodiment, the second classification is indicative of at least one of penetration or aspiration, and the processing module is configured to further classify the swallowing event as a first event indicative of a safe event or a second event indicative of an unsafe event.

In an embodiment, the processing module is configured to classify multiple successive swallowing events by classifying the combined vibrational data for each of the successive swallowing events as indicative of one of the first classification or the second classification.

In an embodiment, the processing module uses a non-segmented spectrogram for pre-processing of at least one of (i) the axis-specific vibrational data along the A-P axis, (ii) the axis-specific vibrational data along the S-I axis or (iii) the combined vibrational data.

In another general embodiment, the present disclosure provides a method for classifying cervical accelerometry data acquired for a swallowing event to identify a possible swallowing impairment in a candidate. The method comprises: receiving axis-specific vibrational data for an anterior-posterior (A-P) axis and a superior-inferior (S-I) axis and representative of the swallowing event, a processing module that is a local or remote computing device operatively coupled to an accelerometer receives the axis-specific vibrational data from the accelerometer; combining at least a portion of a first signal comprising the axis-specific vibrational data for the A-P axis with at least a portion of a second signal comprising the axis-specific vibrational data for the S-I axis using at least one process selected from the group consisting of linear combination, squared (power) sum, moving window correlation of the two signals, local minimum or local maximum of the two signals, and trigonometric relation, the processing module forms the combined vibrational data; and outputting a classification of the swallowing event as one of a plurality of classifications based on the combined vibrational data, the plurality of classifications comprising a first classification indicative of normal swallowing and a second classification indicative of possibly impaired swallowing, and the processing module outputs the classification.

In an embodiment, the method comprises extracting meta-features from the combined vibrational data on the processing module. The method can comprise using the meta-features extracted from the combined vibrational data to classify the swallowing event on the processing module, for example by comparing the meta-features extracted from the combined vibrational data to preset classification criteria to classify the swallowing event on the processing module. The preset classification criteria can be defined for each of swallowing safety and swallowing efficiency and/or defined by features previously extracted and classified from a known training data set.

In an embodiment, the second classification is indicative of at least one of a swallowing safety impairment or a swallowing efficiency impairment.

In an embodiment, the second classification is indicative of at least one of penetration or aspiration, and the method comprises further classifying the swallowing event as a first event indicative of a safe event or a second event indicative of an unsafe event.

In an embodiment, the method comprises classifying successive swallowing events by classifying the combined vibrational data for each of the successive swallowing events as indicative of one of the first classification or the second classification.

In an embodiment, the method comprises using a non-segmented spectrogram for pre-processing of at least one of (i) the axis-specific vibrational data along the A-P axis and the S-I axis or (ii) the combined vibrational data.

In another general embodiment, the present disclosure provides a method of treating dysphagia in a patient. The method comprises: positioning a sensor externally on the throat of the patient, the sensor acquiring vibrational data representing swallowing activity and associated with an anterior-posterior axis and a superior-inferior axis of the throat, the sensor operatively connected to a processing module configured to (i) combine at least a portion of a first signal comprising the vibrational data associated with the A-P axis with at least a portion of a second signal comprising the vibrational data associated with the S-I axis using at least one process selected from the group consisting of linear combination, squared (power) sum, moving window correlation of the two signals, local minimum or local maximum of the two signals, and trigonometric relation and (ii) classify the swallowing event as one of a plurality of classifications based on the combined vibrational data, the plurality of classifications comprising a first classification indicative of normal swallowing and a second classification indicative of possibly impaired swallowing; and adjusting a feeding administered to the patient based on the classification.

In an embodiment, the adjusting of the feeding is selected from the group consisting of: changing a consistency of the feeding, changing a type of food in the feeding, changing a size of a portion of the feeding administered to the patient, changing a frequency at which portions of the feeding are administered to the patient, and combinations thereof.

DETAILED DESCRIPTION

Figure 1:
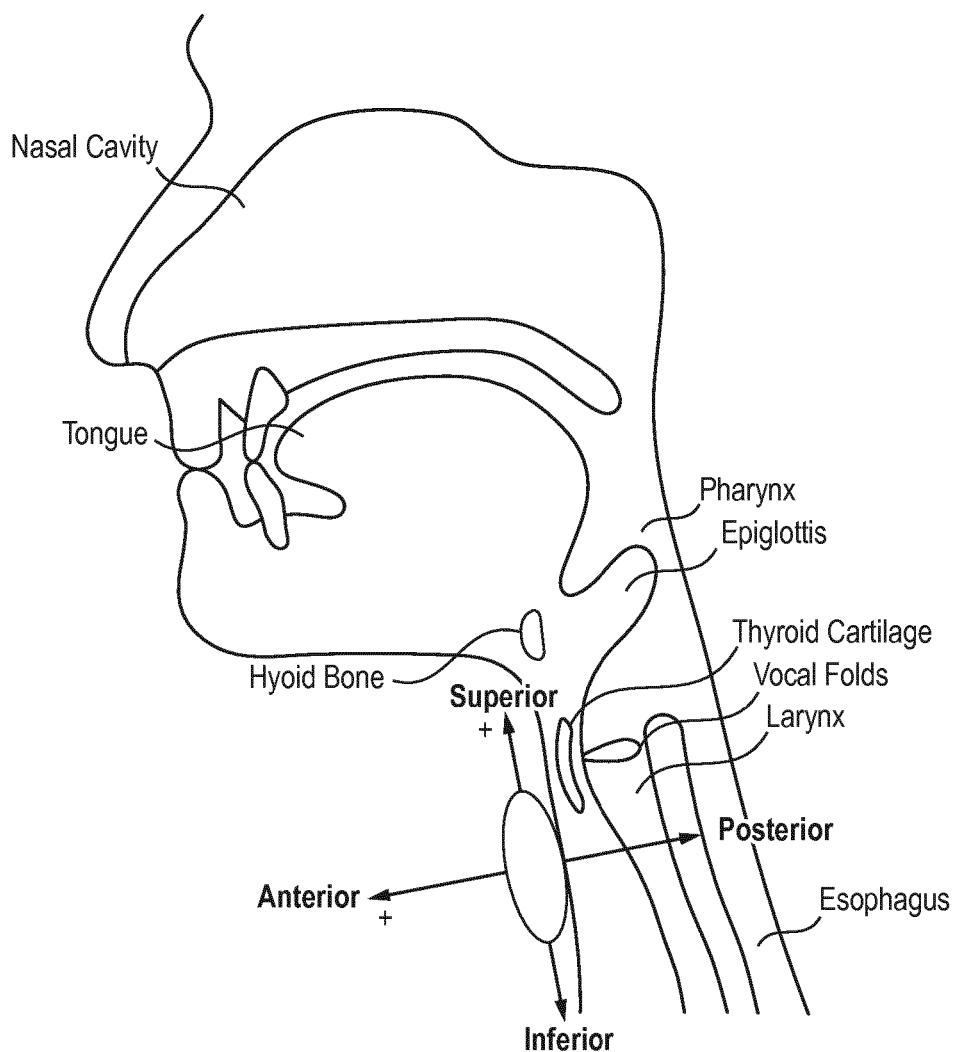
FIG. 1 is diagram showing the axes of acceleration in the anterior-posterior and superior-inferior directions.

As used in this disclosure and the appended claims, the singular forms "a," "an" and "the" include plural referents unless the context clearly dictates otherwise. As used herein, "about" is understood to refer to numbers in a range of numerals, for example the range of −10% to +10% of the referenced number, preferably −5% to +5% of the referenced number, more preferably −1% to +1% of the referenced number, most preferably −0.1% to +0.1% of the referenced number. Moreover, all numerical ranges herein should be understood to include all integers, whole or fractions, within the range.

The words "comprise," "comprises" and "comprising" are to be interpreted inclusively rather than exclusively. Likewise, the terms "include," "including" and "or" should all be construed to be inclusive, unless such a construction is clearly prohibited from the context. A disclosure of a device "comprising" several components does not require that the components are physically attached to each other in all embodiments.

Nevertheless, the devices disclosed herein may lack any element that is not specifically disclosed. Thus, a disclosure of an embodiment using the term "comprising" includes a disclosure of embodiments "consisting essentially of and" consisting of the components identified. Similarly, the methods disclosed herein may lack any step that is not specifically disclosed herein. Thus, a disclosure of an embodiment using the term "comprising" includes a disclosure of embodiments "consisting essentially of and" consisting of the steps identified.

The term "and/or" used in the context of "X and/or Y" should be interpreted as "X," or "Y," or "X and Y." Where used herein, the terms "example" and "such as," particularly when followed by a listing of terms, are merely exemplary and illustrative and should not be deemed to be exclusive or comprehensive. Any embodiment disclosed herein can be combined with any other embodiment disclosed herein unless explicitly stated otherwise.

As used herein, a "bolus" is a single sip or mouthful or a food or beverage. As used herein, "aspiration" is entry of food or drink into the trachea (windpipe) and lungs and can occur during swallowing and/or after swallowing (post-deglutitive aspiration). Post-deglutitive aspiration generally occurs as a result of pharyngeal residue that remains in the pharynx after swallowing.

An aspect of the present disclosure is a method of processing dual-axis accelerometry signals to classify one or more swallowing events. A non-limiting example of such a method classifies each of the one or more swallowing events as a swallow with aspiration-penetration or a swallow without aspiration-penetration. Another aspect of the present disclosure is a device that implements one or more steps of the method.

In an embodiment, the method can further comprise classifying the patient as having safe swallowing or unsafe swallowing. For example, a patient can be classified as having unsafe swallowing if the one or more swallowing events comprise an amount or percentage of aspiration-penetration events that exceeds a threshold. In such an embodiment, the threshold can be zero such that the presence of any aspiration-penetration events classifies the patient as having unsafe swallowing. Of course, in other such embodiments, the threshold can be greater than zero.

In some embodiments, the method and the device can be employed in the apparatus and/or the method for detecting aspiration disclosed in U.S. Pat. No. 7,749,177 to Chau et al., the method and/or the system of segmentation and time duration analysis of dual-axis swallowing accelerometry signals disclosed in U.S. Pat. No. 8,267,875 to Chau et al., the system and/or the method for detecting swallowing activity disclosed in U.S. Pat. No. 9,138,171 to Chau et al., or the method and/or the device for swallowing impairment detection disclosed in U.S. Patent App. Publ. No. 2014/0228714 to Chau et al., each of which is incorporated herein by reference in its entirety.

As discussed in greater detail hereafter, the device may include a sensor configured to produce signals indicating swallowing activities (e.g., a dual axis accelerometer). The sensor may be positioned externally on the neck of a human, preferably anterior to the cricoid cartilage of the neck. A variety of means may be applied to position the sensor and to hold the sensor in such position, for example double-sided tape. Preferably the positioning of the sensor is such that the axes of acceleration are aligned to the anterior-posterior and super-inferior directions, as shown in FIG. 1.

Figure 2:
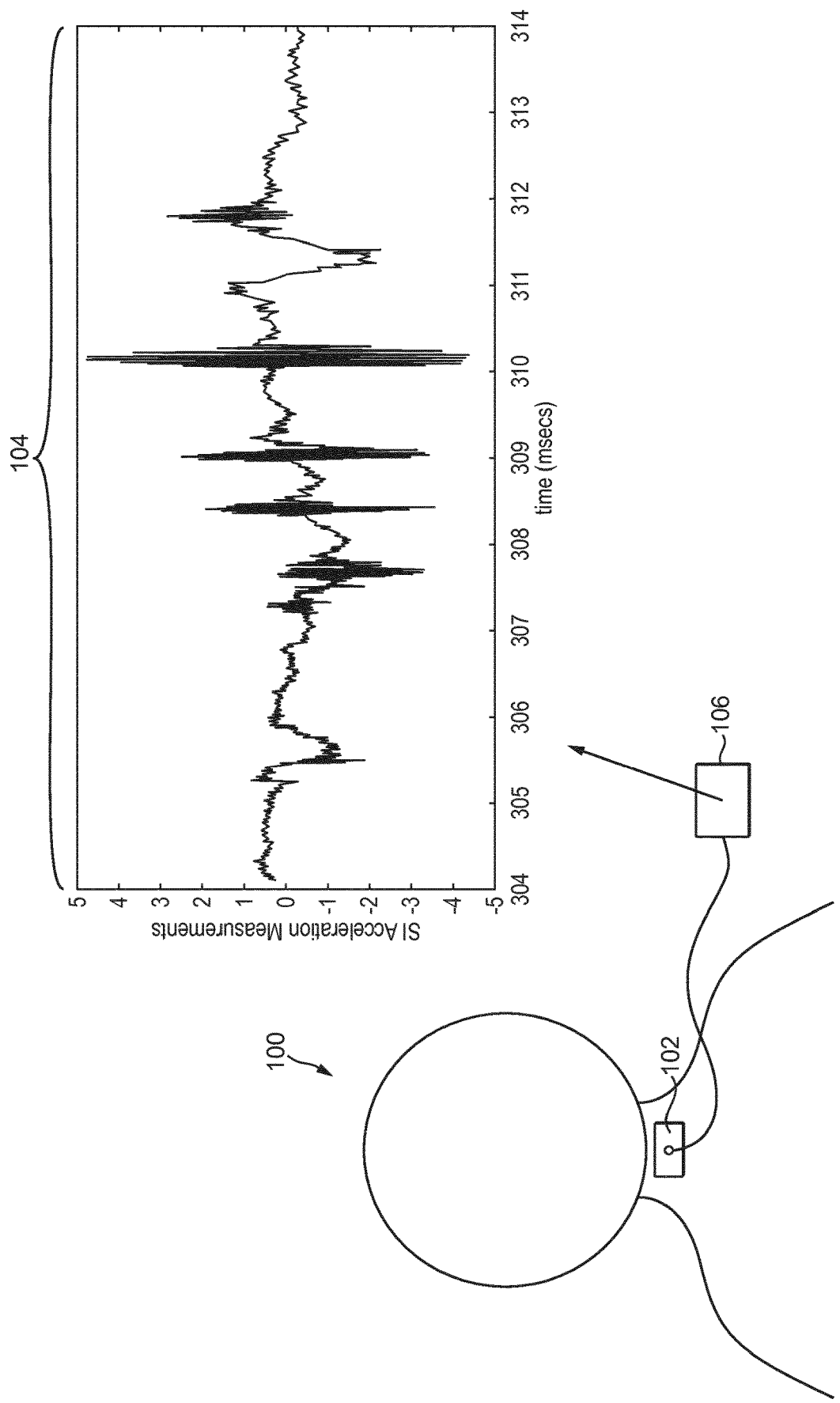
FIG. 2 is a schematic diagram of an embodiment of a swallowing impairment detection device in operation.

FIG. 2 generally illustrates a non-limiting example of a device 100 for use in swallowing impairment detection. The device 100 can comprise a sensor 102 (e.g., a dual axis accelerometer) to be attached in a throat area of a candidate for acquiring dual axis accelerometry data and/or signals during swallowing, for example illustrative S-I acceleration signal 104. Accelerometry data may include, but is not limited to, throat vibration signals acquired along the anterior-posterior axis (A-P) and/or the superior-inferior axis (S-I). As used herein, the anterior-posterior (A-P) axis and the superior-inferior (S-I) axis are relative to the candidate's throat.

The sensor 102 can be any accelerometer known to one of skill in this art, for example a single axis accelerometer (which can be rotated on the patient to obtain dual-axis vibrational data) such as an EMT 25-C single axis accelerometer or a dual axis accelerometer such as an ADXL322 or ADXL327 dual axis accelerometer, and the present disclosure is not limited to a specific embodiment of the sensor 102.

The sensor 102 does not necessarily need to be fixed exactly in A-P and S-I orientation. In this regard, the sensor 102 can merely measure in two perpendicular directions along the sagittal plane of the subject, and the acceleration vectors in both S-I and A-P directions can be extracted from the two sensor signals.

The sensor 102 can be operatively coupled to a processing module 106 configured to process the acquired data for swallowing impairment detection, for example aspiration-penetration detection and/or detection of other swallowing impairments such as swallowing inefficiencies. The processing module 106 can be a distinctly implemented device operatively coupled to the sensor 102 for communication of data thereto, for example, by one or more data communication media such as wires, cables, optical fibers, and the like and/or by one or more wireless data transfer protocols. In some embodiments, the processing module 106 may be implemented integrally with the sensor 102.

Generally, the processing of the dual-axis accelerometry signals comprises combining at least a portion of the axis-specific vibrational data for the A-P axis with at least a portion of the axis-specific vibrational data for the S-I axis using at least one process selected from the group consisting of linear combination, squared (power) sum, moving window correlation of the two signals, local minimum or local maximum of the two signals, and trigonometric relation. The combined accelerometry data can be represented as meta-features, and/or meta-features can be extracted from the combined accelerometry data (e.g., time-frequency meta-features). In a preferred embodiment, a non-segmented spectrogram can be employed in pre-processing. Then the swallowing event can be classified based on the extracted meta-features. In applying this approach, the swallowing events may be effectively classified as a normal swallowing event or a potentially impaired swallowing events (e.g., unsafe and/or inefficient). Preferably the classification is automatic such that no user input is needed for the dual-axis accelerometry signals to be processed and used for classification of the swallow.

Figure 3:
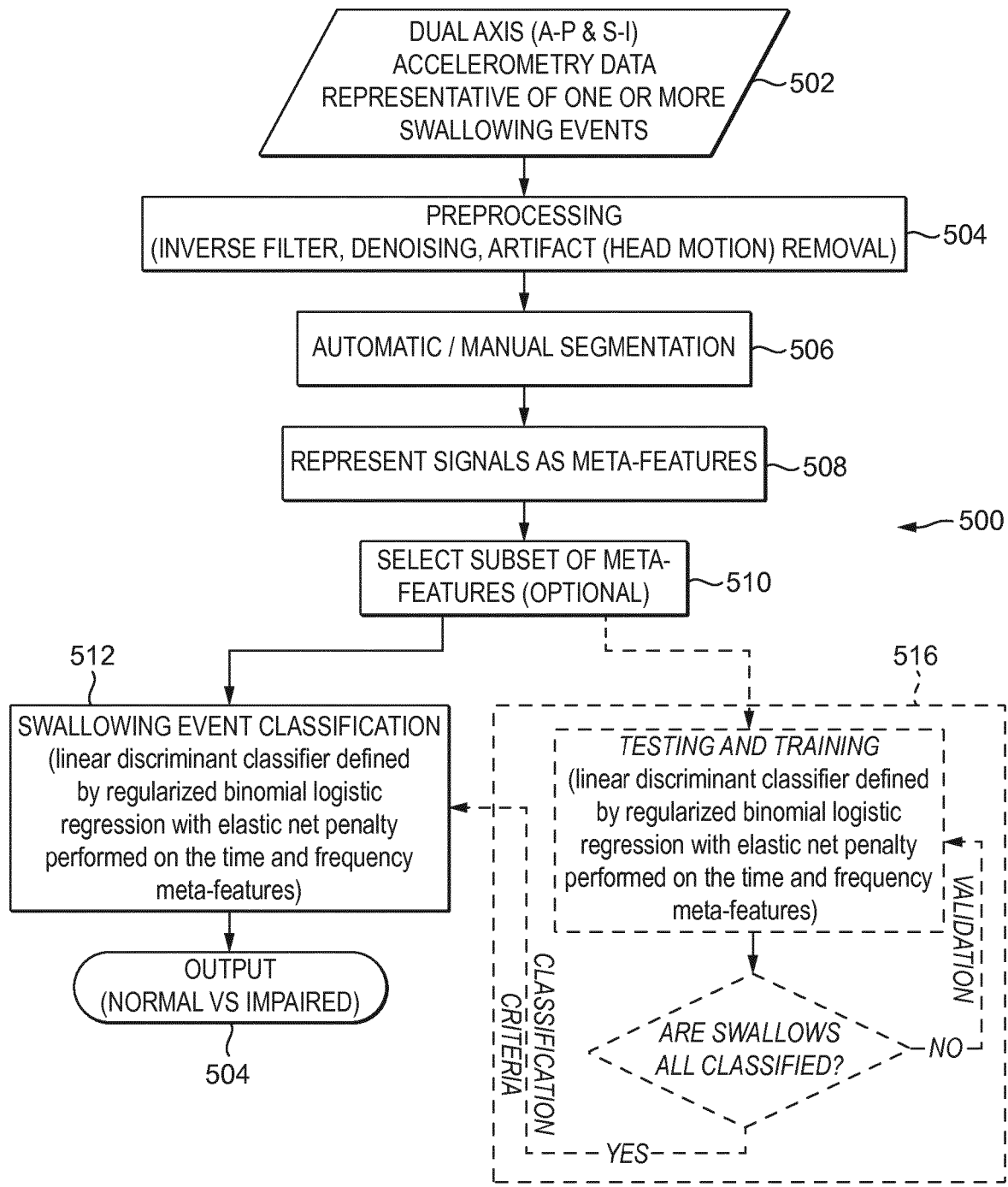
FIG. 3 is a schematic diagram of an embodiment of a method of discriminating swallowing aspiration-penetration.

FIG. 3 illustrates a non-limiting embodiment of a method 500 for classifying a swallowing event. At Step 502, dual-axis accelerometry data for both the S-I axis and the A-P axis is acquired or provided for one or more swallowing events, for example dual-axis accelerometry data from the sensor 102.

At Step 504, the dual-axis accelerometry data can optionally be processed to condition the accelerometry data and thus facilitate further processing thereof. For example, the dual-axis accelerometry data may be filtered, denoised, and/or processed for signal artifact removal ("preprocessed data"). In an embodiment, the dual-axis accelerometry data is subjected to an inverse filter, which may include various low-pass, band-pass and/or high-pass filters, followed by signal amplification. A denoising subroutine can then applied to the inverse filtered data, preferably processing signal wavelets and iterating to find a minimum mean square error.

In an embodiment, the preprocessing may comprise a subroutine for the removal of movement artifacts from the data, for example, in relation to head movement by the patient. Additionally or alternatively, other signal artifacts, such as vocalization and blood flow, may be removed from the dual-axis accelerometry data. Nevertheless, the method 500 is not limited to a specific embodiment of the preprocessing of the accelerometry data, and the preprocessing may comprise any known method for filtering, denoising and/or removing signal artifacts.

At Step 506, the accelerometry data (either raw or preprocessed) can then be automatically or manually segmented into distinct swallowing events. Preferably the accelerometry data is automatically segmented. In an embodiment, the segmentation is automatic and energy-based. Additionally or alternatively, manual segmentation may be applied, for example by visual inspection of the data. The method 500 is not limited to a specific process of segmentation, and the process of segmentation can be any segmentation process known to one skilled in this art.

At Step 508, meta-feature based representation of combined accelerometry data is performed. In a preferred embodiment, at least a portion of the axis-specific vibrational data for the A-P axis can be combined with at least a portion of the axis-specific vibrational data for the S-I axis using at least one process selected from the group consisting of linear combination, squared (power) sum, moving window correlation of the two signals, local minimum or local maximum of the two signals, and trigonometric relation. This processing can occur before any segmentation and/or after any segmentation.

In an embodiment, the dual-axis accelerometry data (e.g., bivariate bolus signals that have been preprocessed and/or normalized) is converted to univariate signals using the windowed inner-product of their A-P and S-I channels with a predetermined window size (e.g., 750 samples) and a predetermined amount of overlap between successive windows (e.g., 90% overlap). The resulting univariate bolus signals (referred to as "inner-product signals" hereafter) can then be represented in terms of meta-features. The meta-feature representation of bolus signals can then be used as the input along with respective labels in subsequent feature selection and/or classification.

At Step 510 (which is optional), a subset of the meta-features may be selected for classification, for example based on the previous analysis of similar extracted feature sets derived during classifier training and/or calibration. For example, in one embodiment, the most prominent features or feature components/levels extracted from the classifier training data set are retained as most likely to provide classifiable results when applied to new test data, and are thus selected to define a reduced feature set for training the classifier and ultimately enabling classification. For instance, in the context of wavelet decompositions, or other such signal decompositions, techniques such as linear discriminant analysis, principle component analysis or other such techniques effectively implemented to qualify a quantity and/or quality of information available from a given decomposition level, may be used on the training data set to preselect feature components or levels most likely to provide the highest level of usable information in classifying newly acquired signals. Such preselected feature components/levels can then be used to train the classifier for subsequent classifications. Ultimately, these preselected features can be used in characterizing the classification criteria for subsequent classifications.

Accordingly, where the device has been configured to operate from a reduced feature set, such as described above, this reduced feature set can be characterized by a predefined feature subset or feature reduction criteria that resulted from the previous implementation of a feature reduction technique on the classifier training data set. Newly acquired data can thus proceed through the various pre-processing and segmentation steps described above (steps 504, 506), the various swallowing events so identified then processed for feature extraction at step 508 (e.g., full feature set), and those features corresponding with the preselected subset retained at step 510 for classification at step 512.

While the above exemplary approach contemplates a discrete selection of the most prominent features, other techniques may also readily apply. For example, in some embodiments, the results of the feature reduction process may rather be manifested in a weighted series or vector for association with the extracted feature set in assigning a particular weight or level of significance to each extracted feature component or level during the classification process. In particular, selection of the most prominent feature components to be used for classification can be implemented via linear discriminant analysis (LDA) on the classifier training data set. Consequently, feature extraction and reduction can be effectively used to distinguish safe swallows from potentially unsafe swallows, and efficient swallows from potentially inefficient swallows. In this regard, the extraction of the selected features from new test data can be compared to preset classification criteria established as a function of these same selected features as previously extracted and reduced from an adequate training data set, to classify the new test data as representative of a normal vs. impaired swallow (e.g., safe swallows vs. unsafe swallows, and/or efficient swallows vs. inefficient swallows). As will be appreciated by the skilled artisan, other feature sets such as frequency, time and/or time-frequency domain features may be used.

At Step 512, feature classification can be implemented. Extracted features (or a reduced/weighted subset thereof) of acquired swallow-specific data can be compared with preset classification criteria to classify each data set as representative of a normal swallowing event or a potentially impaired swallowing event.

In an embodiment, the method 500 can optionally comprise a training/validation subroutine Step 516 in which a data set representative of multiple swallows is processed such that each swallow-specific data set ultimately experiences the preprocessing, feature extraction and feature reduction disclosed herein. A validation loop can be applied to the discriminant analysis-based classifier using a cross-validation test. After all events have been classified and validated, output criteria may be generated for future classification without necessarily applying further validation to the classification criteria. Alternatively, routine validation may be implemented to either refine the statistical significance of classification criteria, or again as a measure to accommodate specific equipment and/or protocol changes (e.g. recalibration of specific equipment, for example, upon replacing the accelerometer with same or different accelerometer type/model, changing operating conditions, new processing modules such as further preprocessing subroutines, artifact removal, additional feature extraction/reduction, etc.).

The classification can be used to determine and output which swallowing event represented a normal swallowing event as compared to a penetration, an aspiration, a swallowing safety impairment and/or an swallowing efficiency impairment at Step 514. In some embodiments, the swallowing event can be further classified as a safe event or an unsafe event.

For example, the processing module 106 and/or a device associated with the processing module 106 can comprise a display that identifies a swallow or an aspiration using images such as text, icons, colors, lights turned on and off, and the like. Alternatively or additionally, the processing module 106 and/or a device associated with the processing module 106 can comprise a speaker that identifies a swallow or an aspiration using auditory signals. The present disclosure is not limited to a specific embodiment of the output, and the output can be any means by which the classification of the swallowing event is identified to a user of the device 100, such as a clinician or a patient.

The output may then be utilized in screening/diagnosing the tested candidate and providing appropriate treatment, further testing, and/or proposed dietary or other related restrictions thereto until further assessment and/or treatment may be applied. For example, adjustments to feedings can be based on changing consistency or type of food and/or the size and/or frequency of mouthfuls being offered to the patient.

Alternative types of vibration sensors other than accelerometers can be used with appropriate modifications to be the sensor 102. For example, a sensor can measure displacement (e.g., a microphone), while the processing module 106 records displacement signals over time. As another example, a sensor can measure velocity, while the processing module 106 records velocity signals over time. Such signals can then be converted into acceleration signals and processed as disclosed herein and/or by other techniques of feature extraction and classification appropriate for the type of received signal.

Another aspect of the present disclosure is a method of treating dysphagia. The term "treat" includes both prophylactic or preventive treatment (that prevent and/or slow the development of dysphagia) and curative, therapeutic or disease-modifying treatment, including therapeutic measures that cure, slow down, lessen symptoms of, and/or halt progression of dysphagia; and treatment of patients at risk of dysphagia, for example patients having another disease or medical condition that increase their risk of dysphagia relative to a healthy individual of similar characteristics (age, gender, geographic location, and the like). The term does not necessarily imply that a subject is treated until total recovery. The term "treat" also refers to the maintenance and/or promotion of health in an individual not suffering from dysphagia but who may be susceptible to the development of dysphagia. The term "treat" also includes the potentiation or otherwise enhancement of one or more primary prophylactic or therapeutic measures. The term "treat" further includes the dietary management of dysphagia or the dietary management for prophylaxis or prevention of dysphagia. A treatment can be conducted by a patient, a clinician and/or any other individual or entity.

The method of treating dysphagia comprises using any embodiment of the device 100 disclosed herein and/or performing any embodiment of the method 500 disclosed herein. The method can further comprise adjusting a feeding administered to the patient based on the classification, for example by changing a consistency of the feeding, changing a type of food in the feeding, changing a size of a portion of the feeding administered to the patient, changing a frequency at which portions of the feeding are administered to the patient, or combinations thereof.

In an embodiment, the method prevents aspiration pneumonia from dysphagia. In an embodiment, the dysphagia is oral pharyngeal dysphagia associated with a condition selected from the group consisting of cancer, cancer chemotherapy, cancer radiotherapy, surgery for oral cancer, surgery for throat cancer, a stroke, a brain injury, a progressive neuromuscular disease, neurodegenerative diseases, an elderly age of the patient, and combinations thereof. As used herein, an "elderly" human is a person with a chronological age of 65 years or older.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method of treating dysphagia in a patient, the method comprising:
    positioning a sensor externally on the throat of the patient, the sensor acquiring vibrational data representing swallowing activity and associated with an anterior-posterior (A-P) axis and a superior-inferior (S-I) axis of the throat, the sensor operatively connected to a processing module configured to (i) combine at least a portion of a first signal comprising the vibrational data associated with the A-P axis with at least a portion of a second signal comprising the vibrational data associated with the S-I axis using at least one process selected from the group consisting of moving window correlation of the two signals, local minimum or local maximum of the two signals, and trigonometric relation to form combined vibrational data and (ii) classify the swallowing event as one of a plurality of classifications based on the combined vibrational data, the plurality of classifications comprising a first classification indicative of normal swallowing and a second classification indicative of possibly impaired swallowing; and
    adjusting a feeding administered to the patient based on the classification.

2. The method of claim 1 wherein the adjusting of the feeding is selected from the group consisting of: changing a consistency of the feeding, changing a type of food in the feeding, changing a size of a portion of the feeding administered to the patient, changing a frequency at which portions of the feeding are administered to the patient, and combinations thereof.

3. The method of claim 1 wherein the sensor measures two sensor signals in perpendicular directions along a sagittal plane of the patient, and the vibrational data associated with the A-P axis and the vibrational data associated with the S-I axis are extracted from the two sensor signals.

4. The method of claim 1 wherein the processing module is configured to extract meta-features from the combined vibrational data.

5. The method of claim 4 wherein the processing module is configured to use the meta-features extracted from the combined vibrational data to classify the swallowing event.

6. The method of claim 5 wherein the processing module is configured to compare the meta-features extracted from the combined vibrational data to preset classification criteria to classify the swallowing event.

7. The method of claim 1 wherein the second classification is indicative of at least one of a swallowing safety impairment or a swallowing efficiency impairment.

8. The method of claim 1 wherein the second classification is indicative of at least one of penetration or aspiration, and the processing module is configured to further classify the swallowing event as a first event indicative of a safe event or a second event indicative of an unsafe event.

9. The method of claim 1 wherein the processing module is configured to classify multiple successive swallowing events by classifying the combined vibrational data for each of the successive swallowing events as indicative of one of the first classification or the second classification.

10. The method of claim 1 wherein the processing module uses a non-segmented spectrogram for pre-processing of at least one of (i) the axis-specific vibrational data along the A-P axis, (ii) the axis-specific vibrational data along the S-I axis, or (iii) the combined vibrational data.

11. The method of claim 1 comprising screening and/or diagnosing the patient based on the classification.

12. The method of claim 1 comprising preventing aspiration pneumonia from dysphagia.

\* \* \* \* \*